United States Patent [19]

Ekins

[11] 4,381,291
[45] Apr. 26, 1983

[54] MEASUREMENT OF FREE LIGANDS

[75] Inventor: Roger P. Ekins, Friday Street, near Dorking, England

[73] Assignee: AB Fortia, Uppsala, Sweden

[21] Appl. No.: 123,328

[22] Filed: Feb. 21, 1980

[30] Foreign Application Priority Data

Feb. 23, 1979 [GB] United Kingdom ................ 7906525

[51] Int. Cl.$^3$ ...................... G01N 33/16; A61K 43/00
[52] U.S. Cl. .......................................... 424/1; 424/1.5; 436/500; 436/518
[58] Field of Search ..................... 424/1, 12; 23/230 B

[56] References Cited

U.S. PATENT DOCUMENTS

| 4,052,504 | 10/1977 | Hertl et al. | 424/1 |
| 4,108,975 | 8/1978 | Hales | 424/1 |
| 4,166,102 | 8/1979 | Johnson | 424/1 |
| 4,225,574 | 9/1980 | Romelli et al. | 424/1 |

FOREIGN PATENT DOCUMENTS

| 878687 | 12/1979 | Belgium | 424/1 |
| 2806860 | 9/1978 | Fed. Rep. of Germany | 424/1 |
| 2396795 | 2/1979 | France | 424/1 |
| 1522566 | 8/1978 | United Kingdom | 424/1 |

Primary Examiner—Benjamin R. Padgett
Assistant Examiner—M. Moskowitz
Attorney, Agent, or Firm—Steele, Gould & Fried

[57] ABSTRACT

A method for indirect measurement of the concentration of a free ligand in a liquid sample also containing the ligand bound to endogenous binding material, comprising the steps of performing two separate measurements, wherein the first measurement is used to determine the total concentration of free and reversibly bound ligand in the sample to be tested, and the second measurement comprises the steps of (i) exposing separately to a known amount of a labelled ligand (a) the sample to be tested, and (b) each of a plurality of standard solutions containing known concentrations of the free ligand, (ii) thereafter exposing each resulting mixture from (i) (a) and (i) (b) separately to an immobilized binding agent to bind a portion of the free labelled ligand and a similar proportion of the free unlabelled ligand to the immobilized binding agent in each mixture, (iii) separating the immobilized binding agent with its bound ligand from the residual material in each mixture, (iv) measuring the proportion of labelled ligand bound to the immobilized binding agent in each mixture, (v) computing, from this proportion and the total concentration of free and reversibly bound ligand determined in the first measurement, the total amount of ligand bound to the immobilized binding agent in each case, and (vi) estimating from this figure the concentration of free ligand in the sample to be tested using as calibration the known concentrations in the standard solutions.

5 Claims, 5 Drawing Figures

MEASUREMENT OF FREE LIGANDS

The present invention relates to the measurement of concentrations of hormones and other ligands present in liquid samples such as body fluids. It provides a general method for the measurement of free ligands present together with bound ligands in such liquids and is particularly concerned with the measurement of free thyroid hormones in blood serum samples. By the term "ligand" as used herein is meant a substance such as a hormone or drug present in a body fluid or other liquid sample and associating with an endogenous binding material such as a protein to form a bound complex, part of the ligand remaining free.

Many hormones found in body fluids are very largely present in bound form, the endogenous binding material being in general a protein, with only a very small proportion of the hormone remaining free. In the case of thyroxine ($T_4$), for example, about 99.99% of the total thyroxine in human blood serum is bound to a mixture of serum proteins, of which the principal component is thyroxine binding globulin (TBG), and only the residual 0.01% is free. Nevertheless it is the concentration of the free form which is thought to be of critical importance because it is this form alone which is believed to interact with the appropriate cell receptors and to be physiologically active. Moreover, variations in the concentration of endogenous binding protein can cause variations in the concentration of free hormone without affecting the total hormone concentration or vice versa. Accordingly, various methods, falling generally into two classes, have been proposed in the past for measurement of the concentration of free hormone.

The so-called indirect methods form the first class. These methods involve two separate measurements on each unknown sample, normally measurement of the total hormone concentration (bound and free) and separate measurement of the fraction of the total that is free, for example by dialysis after addition to the sample of a known amount of radioactively labelled hormone. The product of the two measurements is the concentration of free hormone.

An indirect method has been proposed in British Patent Specification No. 1,522,566 (Corning) for the determination of the concentration of free thyroid hormone in a fluid test sample (otherwise referred to as an unknown sample). That method, as proposed in that specification, comprises performing immunoassays for thyroid hormone on the test (unknown) sample, preferably using antibody for thyroid hormone coupled to a solid support as the binding agent in the immunoassays, in the presence and absence of a blocking agent (a material such as thimerosal or 8-anilino-1-naphthalene-sulphonic acid which displaces the thyroxine from the serum proteins) to establish a binding differential for the test sample—represented by the difference between the percent of thyroid hormone bound with and without the blocking agent in a fixed period of time divided by the percent bound with the blocking agent—and then interpolating that differential onto a standard curve obtained by plotting binding differentials against free thyroid hormone concentrations for standard samples of known free thyroid hormone concentration.

The evaluation stages of that process are based on the assumption that the binding differential is independent of the amount of protein-bound hormone (and binding protein) present in the unknown samples and standard samples being tested, so that samples with the same concentration of free hormones but different concentrations of protein-bound hormone will have the same binding differential. However, this assumption is not justified either in theory or in practice and the process will give correct results only when the concentration of protein-bound hormone in the unknown sample is the same as the concentration in the standard samples from which the standard curve is constructed. When the concentrations are significantly different the estimated free thyroid hormone concentration determined by the method in question has been shown to vary by as much as 50% from the true free concentration.

In contrast, it has been found according to the present invention that it is possible to determine accurately using immobilised binding agent the concentration of free hormone or other ligand in liquid samples also containing bound ligand (i.e. ligand bound to endogenous binding material) by an indirect method taking into account the total concentration of bound ligand.

The so-called direct methods, in which only a single measurement is made on each unknown liquid sample, constitute the second class. One such method involves dialysis of the unknown sample and direct measurement of the amount of hormone in the dialysate. This will be free hormone and as is the case with the indirect method, provided that only a very small proportion of the total hormone in the initial sample is free, the concentration of free hormone in the dialysate will be essentially the same as the concentration in the initial sample, i.e. implicit dilution of the initial sample arising from its contact with the dialysate has no significant effect on the free hormone concentration because some of the initially bound hormone is released in order to maintain thermodynamic equilibrium throughout the system. However, such a dialysis procedure is relatively complex and inconvenient.

A further direct method is disclosed in German Specification DOS No. 2806860 (Lepetit). It involves the extraction of free hormone onto an inert matrix which in broad terms is merely stated to be capable of reversibly adsorbing the free hormone but is in practice a column of a semipermeable inert matrix capable of permitting free hormone into the body of the material, e.g. a natural, synthetic or modified resin, especially a modified crosslinked polysaccharide such as Sephadex, followed by elution of the adsorbed free hormone from the matrix and its subsequent estimation, e.g. by radioimmunoassay. This method essentially comprises a refinement of the direct dialysis procedure in which the semipermeable matrix acts as a substitute for the semipermeable membrane separating the dialysate compartment (the interior of the matrix material in this case) from the sample undergoing dialysis. The matrix is not specific for the individual free hormone and does not react with it but merely acts as a physical extractant. Also, the need for an elution step adds complexity to the process.

A further direct method is disclosed in French Patent Specification No. 2,396,975 (Chandon). This is concerned with the estimation of free hormones or pharmaceuticals by permitting their initial reaction with an antibody followed by assessment of the extent of occupancy of antibody binding sites by backtitration with labelled hormone. For the method use is made of dried solid matrix which in the preferred embodiment is an acrylamide polymer and which contains within the interior of the matrix structure an antibody for the hormone to be estimated, the antibody being present even during the manufacture of the polymer from its monomers. This dry matrix is first contacted with the test sample containing the free hormone, protein-bound hormone and binding protein, and the contact causes the matrix to swell very rapidly. Because of the small size of the pores of the matrix particles only the free hormone, which has a low molecular weight, diffuses into the interior of the matrix particles, whereas the protein-bound hormone and binding protein, which have a larger molecular weight, remain outside. After a very short period of time, about 1 minute in the preferred embodiment, the protein-bound hormone and binding protein are then washed out by means of a solution containing a known amount of radioactivity labelled version of the free hormone. This also diffuses into the matrix particles and a proportion of it becomes bound to the antibody moiety which has not been occupied as a result of binding to the initial free hormone. At the end of a further period, which is a short one—only 10 minutes in the preferred embodiment—because there is no question of equilibration as the reactions are successive according to the specification, the residual unbound labelled hormone is washed out using a buffer solution and the amount of radioactivity remaining on the matrix (bound activity) or appearing in the washed out solution (free activity) is determined. The results obtained with the test sample are compared with a standard curve obtained using samples of known free hormone concentration. In developing such a procedure the inventor clearly relied heavily on the swelling of the particles, leading to separation of free hormone by means of diffusion into the interior of the solid particles, and on preventing the protein-bound hormone from coming into contact with the antibody sequestered within those particles. It is emphasized in the specification that the removal of protein-bound hormone and binding protein by washing should take place as rapidly as possible so that the hormone has no time to diffuse out of the matrix.

In contrast, it has been found according to the present invention that there is no need to sequester the antibody within swellable polymer particles nor to prevent protein-bound hormone contacting the antibody, nor to wash out the bound hormone and subsequently the unbound labelled hormone rapidly.

All the methods mentioned above (apart from the direct dialysis procedure) are comparative methods, i.e. they do not on their own provide measurements of the absolute free ligand concentration but merely provide ways of comparing free ligand concentrations of unknown samples with those of standard samples, regarded in the past as needing to be biological samples containing the same endogenous binding material in broadly similar concentration as well as the same free ligand concentration, and this free ligand concentration in the standard samples must be determined by another, absolute method, whether this is done by the actual user of the standards or by a manufacturer or supplier who then provides the actual user with the standard samples. An absolute method is one which is capable of yielding a measure of free ligand concentration in samples in the absence of a pre-existing method of measuring free ligand concentration. In the case of free thyroxine measurement the direct dialysis procedure does provide an adequate absolute method but this is not universally applicable and for many ligands there is no satisfactory absolute method available. It is noteworthy that neither in British Patent Specification No. 1,522,566 nor in German Application DOS No. 2806860 nor in French Specification No. 2396975, all mentioned above, nor in Belgian Patent Specification No. 878687 (Baxter Travenol) which also discloses a procedure for estimating free ligand concentration by a direct method but was published after the priority date claimed for this patent application, is there any disclosure of a broadly applicable absolute method for standardising the so-called standards.

This presents a problem which is unique to the measurement of free ligand concentrations amongst the measurement of biological substances for clinical purposes and there is a need for a simple solution to the problem. Without a satisfactory absolute method, no comparative method is more than a means for a computing an index which is related to the actual free hormone concentration in some way that cannot be accurately determined, and the methods disclosed in the patent specifications mentioned above are then little more satisfactory than earlier methods for determining such indices, representing at best simpler methods for determining such indices. The disadvantage of such indices is that they are not real physical quantities having an actual meaning, such as a concentration has, but are purely artificial numbers and are influenced by changes in the conditions under which the measurements are made. Thus, they are not reproducible except under identical conditions and results obtained under different conditions cannot be directly compared.

It has been found according to the present invention that it is not necessary to use as standards biologically derived samples of similar composition (content of endogenous binding material and free ligand) whose free ligand concentration has already been determined by another absolute method but that instead it is possible to use as standards solutions made up or standardized by surprisingly simple procedures in a manner not envisaged by other workers in the field.

Essentially the present invention provides a method for the measurement of the concentration of a free ligand in a liquid sample also containing the ligand bound to endogenous binding material, which method includes the steps of bringing the liquid sample into contact with an amount of an immobilised binding agent such that an amount of the free ligand related to the initial concentration of free ligand becomes bound to the immobilised binding agent, and estimating with the aid of a labelled reagent the amount of the ligand bound to the immobilised binding agent, using as a means of calibration the results obtained under the same procedure using standard solutions containing known concentrations of free ligand.

Desirably, but not necessarily, the binding agent will be an antibody specific to the ligand.

The theory upon which the invention is based is that there is an equilibrium in the initial test sample between free ligand (L), binding protein (P) and protein-bound ligand (P-L), which may be represented as follows:

When immobilised binding agent (hereinafter referred to for convenience as immobilised antibody or $\overline{\text{I-Ab}}$) is added a further reaction occurs This second reaction, by removing a proportion of the initially free ligand, disturbs the first equilibrium. However, if the amount of immobilised antibody added is sufficiently small that the concentration of the antibody-bound moiety ($\overline{I\text{-}Ab}$-L) is small relative to the protein-bound moiety (P-L), the addition of the antibody will not significantly alter the initial concentration of free and bound ligand and only the second reaction need be considered. The reaction follows second order kinetics so that the rate at which the free ligand is bound to the binding agent is governed by the initial concentration of free ligand. Ultimately, an equilibrium between free ligand and antibody is established having an equilibrium constant K which may be represented as follows:

$$K = \frac{[\overline{I - Ab} - L]}{[\overline{I - Ab}][L]}$$

$$[L] = \frac{1}{K} \cdot \frac{[\overline{I - Ab} - L]}{[\overline{I - Ab}]}$$

where [L] is substantially equal to the initial free ligand concentration prior to addition of the immobilised antibody. The practical implication of the equation is that, by estimating (when equilibrium has been obtained) the occupancy of antibody binding sites by observation either of the amount of ligand bound to them or of the amount of residual (unoccupied) sites, the concentration of free ligand in the test sample may be estimated.

Moreover, it may also be shown that prior to the attainment of thermodynamic equilibrium the fractional occupancy of antibody binding sites is related to the free ligand concentration by the following equation:

$$\frac{[\overline{I - Ab} - L]}{[\overline{I - Ab}] + [\overline{I - Ab} - L]} = \frac{K[L](1 - e^{-K_d T(K[L]+1)})}{K[L] + 1}$$

where T is time and $K_d$ is the dissociation rate constant of the immobilised antibody. The validity of this equation rests on the assumption that the rate at which ligand binds to the specific antibody is not restricted by the rate at which the ligand dissociates from the endogenous binding material present in the test sample.

The choice as to whether measurements are made before or after establishment of equilibrium will be dependent on a variety of factors such as the concentration of the free ligand, the characteristics of the antibody and the time-scale within which the assay is to be completed, the aim being generally to maximise the precision and convenience of the assay.

In one of its aspects the present invention is characterised by the method employed to provide appropriate samples for use as standard samples of known free ligand concentration so that an absolute value for the free ligand concentration in the test samples can be determined. The standard samples characteristic of the prior art were biological samples containing endogenous binding material which binds a major proportion of the total ligand concentration to form a complex which in turn liberates free ligand by dissociation as the free ligand concentration otherwise tends to fall owing to binding to immobilised binding agent, so that the overall free ligand concentration remains substantially unaffected. By contrast, the primary standard samples of this aspect of the present invention do not contain such a reservoir of ligand bound to endogenous binding material.

Such primary standard solutions may be solutions containing predetermined (e.g. weighed) or measured (e.g. by extinction) initial concentrations of ligand. In that event they may be used as standards by incubating an amount of the immobilised binding agent corresponding to the amount used in the test on the unknown sample with relatively large volumes of the standard solutions such that the concentration of free ligand remaining in the relatively large volume of solution is not significantly altered during the incubation. For different standard solutions different weighed amounts of free ligand and/or different volumes of solution are used. The incubation with the relatively large volume of solution is either carried out until equilibrium is reached or, as with the incubation of the unknown samples, is terminated before equilibrium has been reached, but in the latter event the incubation period should then be the same as the incubation period with the unknown sample. Other incubation conditions should be identical for the relatively large volumes and the unknown samples for optimum results.

The extent to which the relatively large volume of solution used for the standards exceeds the volume of the unknown sample for best results is dependent on the fraction of the ligand which is bound in the unknown sample.

Preferably, the volumes used for the standard solutions are each approximately equal to the volume of the unknown sample divided by the fraction of the ligand in the unknown sample which is free. The volume ratio is unlikely in any event to be less than 10:1 and will in many cases be in the range 100:1 to 10,000:1. For thyroxine it is preferably of the order of 1,000:1. The objective is to use a sufficiently large volume that the depletion in the concentration of ligand during the incubation of the standard is comparable with the depletion in ligand concentration in the unknown sample during its incubation, say 2-3% in each case.

The concentrations of the free ligand in the standards should be chosen with a view to providing good calibration of the results achieved with the unknown samples. In other words the concentrations in the standards should lie generally in the same range as in the unknown samples but encompassing the likely extremes and providing a reasonable scatter between. Generally speaking at least 4 different standard solutions will be required and 6-10 is often the appropriate range.

Of course, it will be appreciated that the procedure in question (use of a relatively large volume to make a primary standard) need not be performed be every user of the technique. Instead the procedure may be used to calibrate secondary standards which are then employed as the standards by the ultimate user.

Instead of using such a method of making up primary standards it is possible actually to measure the concentration of free ligand in standard solutions containing free ligand but not ligand bound to endogenous binding material after they have been used in the estimation procedure, i.e. after they have been incubated with immobilised antibody. Such a method avoids the need to use relatively large volumes for the standard solution and permits the use of samples comparable in volume with the test samples but has in turn the requirement that it can only be used when it is possible to reach thermodynamic equilibrium between the ligand in the solution and the ligand on the immobilised binding agent (antibody).

This post-incubation concentration of free ligand in the standard solutions may be determined by removing the solutions from the immobilised binding agent and measuring the concentration using an immunoassay technique employing as further standards solutions containing known concentrations of free ligand (in the absence of binding agent) made up by a weighing procedure. Alternatively by employing labelled (e.g. radioactively labelled) ligand in the standards the proportionate depletion of the labelled ligand concentration in the standards as a result of the incubation with the immobilised binding agent can be measured so that, knowing the initial concentration, the final concentration can be calculated.

It will be appreciated that these methods of preparing the standard solutions or of determining the post-incubation free ligand concentration are applicable equally to direct and indirect methods for determining free ligand content. They may be used with the methods described hereinafter and for other methods of the general type covered by the invention, including if so desired the erroneous method disclosed in British Patent Specification No. 1,522,496 and the methods disclosed in German Specification DOS No. 2806860, French Patent Specification No. 2396975 and Belgian Patent Specification No. 878687 mentioned above.

The standard samples provided according to each of the procedures of this aspect of the invention have the common feature that they do not contain a reservoir of ligand bound to endogenous binding material. Such a reservoir, which is invariably present in natural samples, has the effect of keeping the concentration of the free ligand in the standard samples substantially constant during the incubation, for the reasons (and subject to the constraints) mentioned above, and samples containing such a reservoir can be said to be self-replenishing. Bearing in mind that the unknown test samples will be self-replenishing, there would be a natural tendency, amongst those people who even go as far as to become aware of or think about the problem of standard samples and their provision, to assume that the standard samples also need to be self-replenishing. This tendency would prejudice such people against artificial standards which do not contain ligand bound to endogenous binding material. However, the prejudice that would result is a mistaken one and it is perfectly possible as explained above to make up and use standards which are not self-replenishing in this way and to obtain accurate absolute values for the free ligand concentration in the unknown test samples with their aid.

According to a second aspect of the invention I provide an improved process for the direct measurement of free ligand concentration. Such a process is additionally characterised by separately exposing the unknown liquid sample to be tested (containing free ligand and endogenously-bound ligand, i.e. ligand bound to endogenous binding material) and standard liquid samples (containing free ligand at a concentration following the exposure step which is known or measured) to binding agent specific for the ligand in a manner permitting direct contact between endogenously-bound ligand and immobilised binding agent, separating the immobilised binding agent (including ligand bound thereto as a result of the exposure) from the residual liquid containing free ligand and endogenously-bound ligand, subsequently adding a labelled reagent to the immobilised binding agent and measuring, by investigation of the distribution of the labelled reagent, the amount of ligand from the initial sample and standard samples that has become bound to the immobilised binding agent.

When the ligand molecule is small, for example with a molecular weight up to about 1,000, so that it will not participate in "sandwich" formation in which the endogenously bound ligand is bound to the immobilised binding agent or the ligand bound to the immobilised binding agent is also bound to another binding agent, the measurement will involve back-titration (i.e. measurement of unoccupied sites on the immobilised binding agent) with a labelled (e.g. radioactively labelled) ligand interacting with the same antibody sites, preferably with the same ligand in labelled form. When the ligand molecule is larger, for example with a molecular weight over 1,000, so that "sandwich" formation can occur, it is possible to use direct titration (i.e. measurement of occupied sites on the immobilised binding agent) with a labelled (e.g. radioactively labelled) binding agent interacting with the ligand. This method is essential if the endogenously-bound ligand in the initial sample is itself capable of binding to the antibody, thus forming a "sandwich", because in these circumstances the occupancy of the sites on the immobilised binding agent will not reflect the true free ligand concentration in the initial sample.

The back-titration procedure conveniently comprises the following steps (the term "antibody" being used as short for "binding agent");

(a) separating immobilised unbound and ligand-bound antibody from the remainder of the liquid sample, (b) bringing the separated immobilised antibody into contact with a liquid containing a known amount of a labelled ligand, whereby a proportion of the labelled ligand becomes bound to the immobilised antibody, (c) separating the immobilised unbound and (labelled and unlabelled) ligand-bound antibody from the remainder of the liquid, (d) determining the amount of labelled ligand bound to the immobilised antibody, and (e) estimating therefrom the amount of unlabelled ligand initially bound to the immobilised antibody and/or the amount of free ligand in the initial sample, using as calibration results obtained from standard liquid samples containing known concentrations of free ligand. These standard samples may either comprise buffer solutions lacking endogenous binding material and prepared or evaluated according to the first aspect of the present invention described above or may be secondary standards containing endogenous binding material and prepared and calibrated in the traditional manner.

When the measurement of ligand bound to immobilised binding agent is by means of a back-titration procedure, the immobilised binding agent should be specific to the ligand, at least as compared to other possible ingredients of the samples, otherwise errors will be introduced. It should also have a high affinity for the ligand, preferably a binding constant (i.e. equilibrium constant for the binding reaction) which is comparable with the reciprocal of the free ligand concentration in the unknown test samples, more preferably approximately equal to this reciprocal or within a factor of 5 of it. In the case of thyroxine it is best to use an immobilised binding agent having a binding constant of more than $10^9$ liters per mole. When the measurement of ligand bound to immobilised binding agent is by means of a direct titration, using a labelled binding agent, either the labelled binding agent or the immobilised binding agent should be specific to the ligand, at least as compared to other possible ingredients of the samples, to avoid errors, and preferably but not necessarily both are specific to the ligand. However, neither of the two binding agents in this situation need have such a high affinity as the immobilised binding agent for the back-titration procedure, although they may do so. Preferably the binding agent is an antibody, especially for the back-titration procedure. Antibodies for a wide variety of hormones are known and are usually commercially or otherwise readily available.

The immobilised binding agent may be coupled to the surface of solid inert support particles, for example of cellulose, polysaccharide (e.g Sephadex—Trade Mark) or glass, which are free to move in the liquid sample. Alternatively, but not necessarily with equal success, the binding agent may be immobilised by attaching it to the wall of the vessel, e.g. test tube or the like, in which the estimation is carried out and to which the liquid sample is added. Techniques for immobilising binding agents are known. All that is required is that the binding agent should in some way be made readily separable from the liquid sample by solid-liquid separation techniques such as decantation, centrifugation or the like. It is neither necessary nor desirable that the binding agent should be sequestered within the interior of a polymer or gel matrix as this only introduces further complicating factors of preferential diffusion which are unnecessary and irrelevant to accurate determination of the concentration of free ligand. Therefore, according to the invention the binding agent should be immobilised on the surface of the support material.

The use of free moving support particles for the binding agent has the advantage over the use of a vessel coated on its internal surface with binding agent that the amount of antibody used may be accurately standardised. Also it may be easily varied to accommodate the measurement of biological samples of exceedingly small size, e.g. filter paper spot samples. The achievement of optimum results by use of the method depends on the achievement of sufficient mixing of binding agent and liquid so that the concentration of free ligand in the immediate vicinity of the binding agent is maintained substantially constant during the course of the reaction unless the reaction is allowed to proceed to equilibrium. By having free moving support particles for the binding agent the opportunity for concentration gradients to arise within the liquid is reduced.

The amount of immobilised binding agent to be used (expressed in terms of its binding site capacity) should be small relative to the amount of endogenously-bound ligand, at least when employing a back-titration procedure. When employing direct titration, on the other hand, it would be possible to use relatively larger amounts of lower affinity immobilised binding agent. The optimal amount will depend on the relative proportions of the ligand which are initially free and endogenously-bound, i.e. the affinity of the endogenous binding material for the ligand, and the relative proportions of free ligand and ligand which becomes bound to the immobolised binding agent, i.e. the affinity of the immobilised binding agent for the ligand. Generally speaking, however, the amount of binding agent introduced should be such as will not substantially alter the concentration of free ligand. In many cases this alteration will be less than about 10% of the initial concentration, although larger alternations may be tolerable in certain circumstances.

Normally the direct method is carried out using diluted test samples, the dilution being for example from 1 in 2 to 1 in 50. However, in some instances, for example when the effect of certain endogenous or exogenous materials on free ligand concentration is being investigated or when investigating samples in which the proportion of endogenously bound ligand is relatively low, it may be desirable to work with undiluted test samples. The direct method can in principle be used with such samples although special care may be needed because of problems arising from the viscosity of the solution etc.

The direct measurement method of the present invention has many advantages. It can be used on liquid samples which are very small indeed, e.g. of the order of 2 micro-liters, such as heel pricks taken from 5-day old babies being tested for thyroid hormone deficiency leading to cretinism. More importantly, because the concentration of free hormone is largely unaffected by dilution within reasonable limits unless there are special circumstances (e.g. presence or introduction of special factors affecting free ligand concentration), the exact volume of the sample taken is not critical. Hence it is ideal as a method for assaying dried blood samples held on filter paper, the filter paper being suspended in buffer to form the liquid sample.

According to a third aspect of the present invention there is provided an improved and corrected indirect method for the determination of free hormone concentration. This indirect method is additionally characterised in that for the unknown liquid sample and each standard solution two separate but related measurement operations are performed, one of these operations resulting in the determination of the total concentration of free and reversibly bound ligand in the unknown sample and the other operation comprising exposing separately the unknown sample and each standard solution to a known amount of labelled (e.g. radioactively labelled) ligand, thereafter exposing each resulting mixture separately to immobilised binding agent to bind a proportion of the free labelled ligand and a similar porportion of the free unlabelled ligand to the immobilised binding agent, separating the immobilised binding agent with its bound ligand from the residual solution, measuring the proportion of labelled ligand bound to the immobilised binding agent, computing from this proportion and the known total concentration of free and reversibly bound ligand the total amount of ligand bound to the immobilised binding agent in each case and estimating from this figure the concentration of free ligand in the unknown sample using as calibration the known concentrations in the standard solutions.

Conveniently and preferably the total concentration of free and reversibly bound ligand in the unknown sample is also measured by means of a similar assay operation, differentiated from the preceding assay by the fact that the initial separate exposures of the unknown sample and standard solutions to the labelled ligand are each carried out in the presence of a so-called blocking agent for the reversibly bound ligand.

A blocking agent in this context is any material which effectively causes reversibly bound ligand to dissociate from its endogenous binding material, e.g. binding protein so that it is all available to bind to the immobilised binding agent in the subsequent step. Blocking agents of this type are known for a variety of ligands. Thus, for example, 8-anilino-1-naphthalenesulphonic acid (ANS)

and thimerosal are effective blocking agents for thyroxine, triiodothyronine and several other ligands reversibly bound to binding proteins. Some blocking agents may not be effective to cause all the endogenously bound ligand to dissociate from the endogenous binding material, as is the case with insulin, for example, or at least may only cause all of it to dissociate over a very extended period. However, this need not prevent their use as blocking agents because the residual bound ligand then has, in general, no effect on the results obtained. It is in this context that the term "reversibly bound ligand" is used to denote ligand which can be readily and rapidly dissociated from endogenous binding material and thus participates in exchange with labelled ligand and dissociates in the presence of blocking agent.

In this third aspect of the invention, as in the second aspect of the invention, the standard solutions may comprise buffer solutions lacking endogenous binding material but prepared or evaluated according to the first aspect of the invention or they may be secondary standards containing endogenous binding material and prepared and calibrated by traditional methods. The immobilised binding agent used in this aspect of the invention need not be specific for the ligand nor need it have a high affinity for it. However, it may be convenient to use an immobilised antibody specific to the ligand. The remarks made under the heading of the second aspect of the invention about the nature of the support for the immobilised binding agent and the amount of immobilised binding agent for the measurement operations apply to this aspect of the invention also.

It will be appreciated that, by first estimating the effective total concentration of free and reversibly bound ligand and then using this to compute the actual amount of ligand bound in the second operation before estimating from this figure the free ligand concentration, allowance is made for changes in the concentration of endogenously-bound ligand (which also participates in exchange with the labelled ligand) between the standards and the unknown sample and amongst the standards themselves. The method thus gives correct results in situations where the method disclosed in British Patent Specification No. 1,522,596 gives incorrect results and its use on kits constructed for use according to that latter method enables those kits to be used successfully.

As compared with the direct method the indirect method has the advantage that:

(i) it yields an estimate of both total ligand and free ligand and both of these may be useful diagnostically;

(ii) it is not critically dependent on the use of a binding agent with high binding constant (affinity) or specificity; and (iii) it may be technically easier to perform.

The direct method, on the other hand, has the advantages that:

(i) it requires only a single sample whose volume need not be precisely known;

(ii) there is no need to equilibrate labelled ligand with endogenous ligand as a part of the procedure;

(iii) it does not require measurement of total ligand content and (iv) it does not require the availability of labelled ligand identical in chemical form to the unlabelled ligand being estimated, and thus opens the way to using enzyme-labelled, fluorescein-labelled and other labelled ligand and enables the use of potentially environmentally harmful radioisotopes to be reduced.

In all three of its aspects the present invention is of particular importance for the determination of free thyroxine ($T_4$) in the presence of naturally-occurring binding proteins. It can also be used for the determination of other free hormones in the presence of naturally-occurring binding proteins, e.g. for triiodothyronine ($T_3$), aldosterone, testosterone and cortisol. Most hormones in such a situation are bound to the extent of 60% or more.

The invention can additionally be used for the determination of free hormones in the presence of hormone-binding antibodies which are present as a result of disease, for example, free insulin or thyroxine in blood containing insulin antibodies or thyroxine antibodies as the case may be.

Furthermore, in certain circumstances the invention can be used for the determination of ligands of other types, e.g. vitamins, such as vitamin D and vitamin B12, drugs, present in free form in small quantities in liquid samples together with their bound form, usually a protein-bound form.

Generally, the samples to be tested will be samples derived from a body fluid, e.g. serum samples, of a living creature, most frequently a human patient, and the free ligand whose concentration is to be estimated will be a compound occurring in free and bound form in that body fluid either naturally or as a result of a particular medical regimen.

The following Examples illustrate the application of the invention in its second and third aspects to the determination of free thyroxine ($T_4$) and triiodothyronine ($T_3$), as well as the first aspect of the invention.

Reagents (1) Thyroxine ($T_4$) antiserum, H/t/28, was purchased from RAST Allergy Unit, Benenden, Kent. It had been raised in sheep, its equilibrium constant K was $2 \times 10^{11}$ liters/mole, and its binding site concentration was 16.2 µg thyroxine/ml.

(2) Triiodothyronine ($T_3$) antiserum, S177, was raised in the Department of Nuclear Medicine, Middlesex Hospital Medical School. It had been raised in sheep, its equilibrium constant K was $1.1 \times 10^{11}$ liters/mole.

(3) Cellulose—microcrystalline, purchased from Merck—was activated with cyanogen bromide by the method described by L. Wide ("Radioimmunoassay Employing Immunosorbents" in "Immunoassay of Gonadotrophins", Karolinska Symposia on Research Methods in Reproductive Endocrinology, ed. Diczfalusy E., pages 207-221 (1969) Stockholm). The $T_4$ antibody was coupled to the cellulose as described by L. Wide (op. cit.) 100 µl of serum was coupled to 600 mg of cellulose.

(4) Polysaccharide (=Sephadex), ultrafine, from Pharmacia Diagnostics AB, was used to couple the $T_3$ antibody; 50 µl of serum was coupled to 100 mg of Sephadex.

(5) High specific activity thyroxine (L-[3', 5'-$^{125}$I]-thyroxine), specific activity greater than 1200 µCi/µg, was purchased from The Radiochemical Centre, Amersham, Bucks.

(6) High specific activity $^{125}$I-triidothyronine, specific activity greater then 1200 µCi/µg, was purchased from The Radiochemical Centre, Amersham, Bucks.

(7) The buffer used was HEPES (N-2-hydroxyethyl-piperazine-N'-2-ethanesulphonic acid), 0.01 mole/liter, pH 7.4, with NaCl, 6.2 g/l, and sodium azide, 0.065 g/l. (Where indicated 8-anilino-1-naphthalenesulphonic acid (ANS), bovine serum albumin and TWEEN 20 were added to this buffer.)

(8) Sera calibrated by equilibrium dialysis so that their free $T_3$ or $T_4$ concentrations were known were used as standardised sera in Examples 1-3, their total $T_3$ or $T_4$ concentrations also being known.

EXAMPLE 1

(Direct $T_4$ assay)

A typical assay involves the following steps:

(1) 100 μl samples of standardised sera and unknown sera are pipetted into separate assay tubes.

(2) 800 μl of cellulose-anti $T_4$ suspension in HEPES buffer is added to each tube and the tubes are vortexed and incubated at room temperature for one hour. (800 μl of cellulose-anti $T_4$ suspension contains 400 μg of cellulose coupled to 0.067 μl of $T_4$ antiserum with a $T_4$ binding site concentration of 1.08 ng.)

(3) After the incubation step about 1.5 ml of ice-cold HEPES buffer containing bovine serum albumin, 1 g/l, and TWEEN 20, 1 g/l, is added and the tubes are vortexed briefly and then centrifuged for one minute at 1500 G. All but 0.3 ml of the supernatant liquid is aspirated and discarded. Two further washes with 2.0 ml of buffer are performed.

(4) To each tube is then added 100 μl of buffer containing bovine serum albumin and TWEEN 20 as in step (3) and also containing approximately 40,000 cpm of $^{125}$I-labelled thyroxine ($T_4$). The tubes are vortexed and incubated at room temperature for 30 minutes.

(5) After the incubation period about 2 ml of ice-cold buffer containing bovine serum albumin and TWEEN 20 as in step (3) is added, the tubes are centrifuged at 1500 G for 5 minutes and the supernatant is removed by decanting and discarded.

(6) The bound radioactivity is then counted. A standard curve is prepared from the values for standardised sera and the free $T_4$ concentrations in the unknown sera obtained from this curve.

Figure 1:
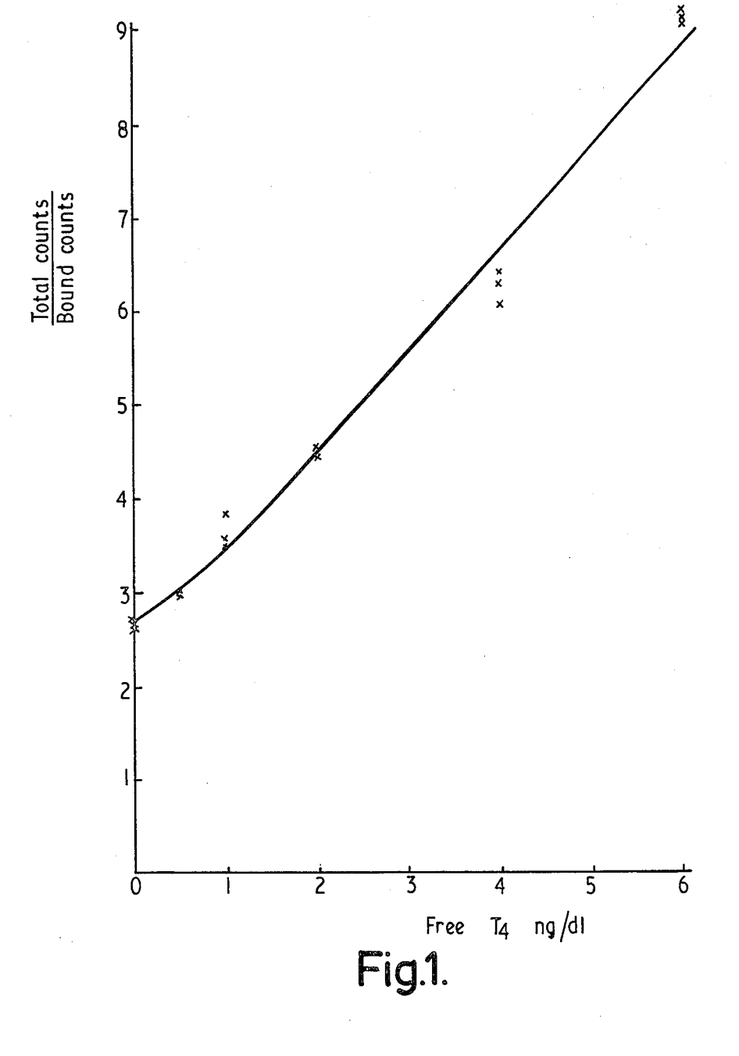

A standard curve is shown in FIG. 1 of the accompanying drawings. In it the ratio of total counts to free counts, as ordinate, is plotted against the free thyroxine concentration in ng/dl, as abscissa. In the test the total counts amount to 39,165 cpm and the non-specific counts to 140 cpm. Some results for a variaty of unknown samples estimated in this way are given in Table 1.

TABLE 1

| | Known clinical status | Total counts ÷ Bound counts | Free $T_4$ ng/dl |
|---|---|---|---|
| 1. | Hypothyroid | 2.95 | 0.5 |
| 2. | Hypothyroid | 2.8 | 0.3 |
| 3. | Hypothyroid | 2.9 | 0.45 |
| 4. | Euthyroid, pregnant | 3.7 | 1.20 |
| 5. | Euthyroid, high TBG | 4.35 | 1.85 |
| 6. | TBG deficiency | 4.5 | 2.0 |
| 7. | Hyperthyroid | 6.4 | 3.85 |
| 8. | Hyperthyroid | 7.28 | 4.70 |
| 9. | Hyperthyroid | 6.05 | 3.50 |

We have found that variation of the serum sample size in the range from 50 to 200 μl does not alter the standard curve.

EXAMPLE 2

(Indirect $T_4$ assay)

A typical assay involves the following steps:

(1) 25 μl samples of standardised sera and unknown sera are pipetted into separate assay tubes in each of two series.

(2) Into each tube of the first series of tubes 100 μl of HEPES buffer containing 500 μg of ANS and approximately 40,000 cpm of $^{125}$I-labelled $T_4$ is added and the tubes are vortexed and incubated for 20 minutes at room temperature.

(3) 800 μl of cellulose-anti $T_4$ suspension in HEPES buffer (as defined in Example 1) is added to each tube in this series, and the tubes are vortexed and incubated at room temperature for 30 minutes.

(4) After the incubation approximately 1.5 ml of ice-cold HEPES buffer containing bovine serum albumin, 1 g/l, and TWEEN 20, 1 g/l, is added to each tube in this series, and the tubes are vortexed and centrifuged at 1,500 G for 5 minutes. The supernatant is decanted and discarded and the bound radioactivity counted.

(5) A standard curve is prepared from the values obtained from the standardised sera and the unknown total thyroxine concentrations obtained from this curve.

(6) In parallel with step (2) 100 μl of HEPES buffer containing approximately 40,000 cpm of $^{125}$I-labelled thyroxine is added to each tube in the second series of tubes, which are then vortexed and incubated for 20 minutes at room temperature.

(7) Step (3) is performed for this series of tubes.

(8) Step (4) is performed for this series of tubes.

(9) For the standard sera a curve is prepared in which the free $T_4$ concentrations are plotted against the amounts of $T_4$ in the tubes which have been bound by cellulose-anti $T_4$. The amount of $T_4$ bound is computed by multiplying the fraction of $^{125}$I-labelled thyroxine that is bound by the total amount of $T_4$ in the sample. For the unknown sera the total $T_4$ is first determined from step (5), then the amount of $T_4$ bound is computed and the free $T_4$ concentration determined from the standard curve.

Figure 2:
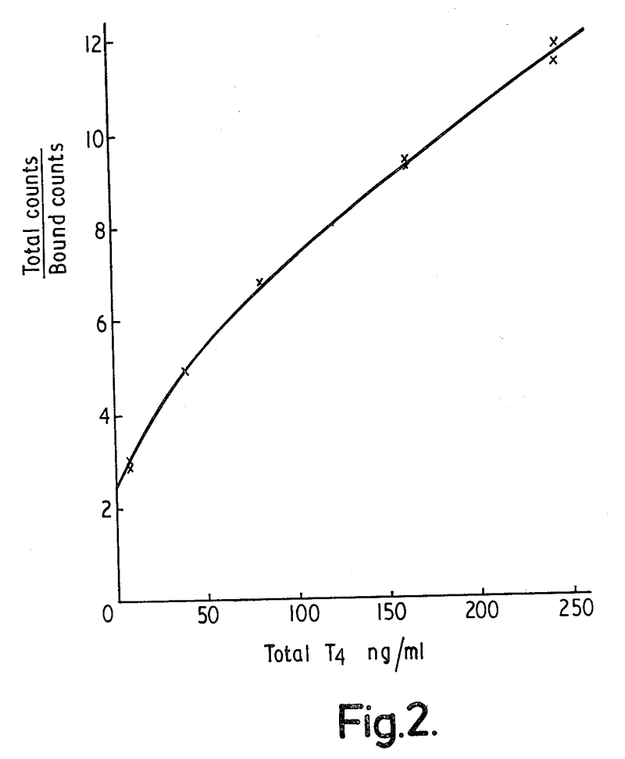
Figure 3:
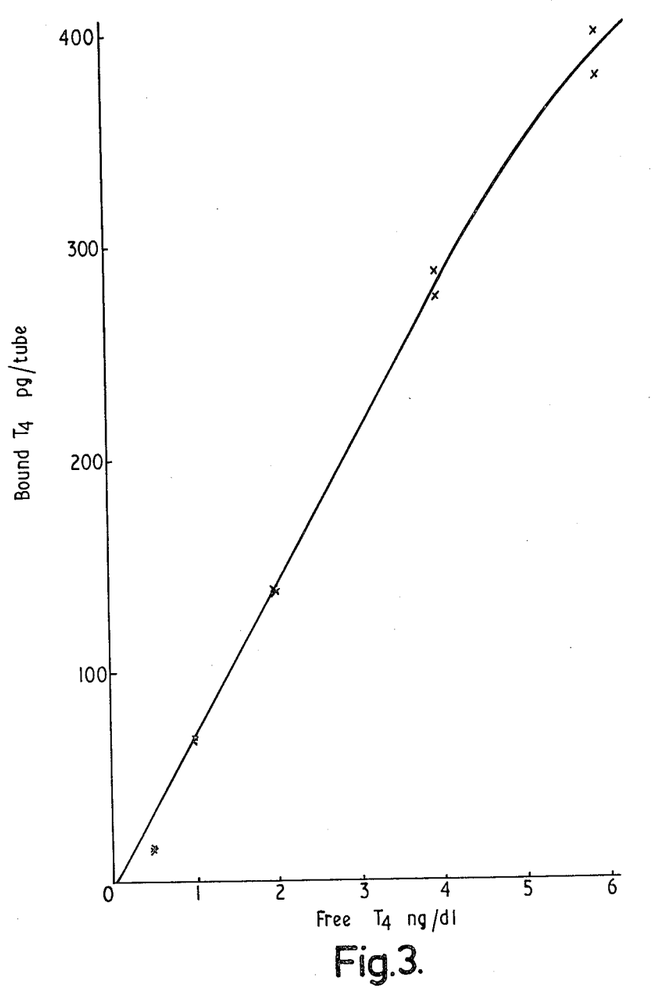

A standard curve for estimation of total $T_4$ is shown in FIG. 2 of the accompanying drawings, the ratio of total counts to bound counts being plotted against total thyroxine concentration in ng/ml. FIG. 3 of the accompanying drawings is a standard curve for the estimation of free $T_4$, bound $T_4$ in pg/tube being plotted against free thyroxine concentration in ng/dl.

The method of calculation is shown for one unknown sample (in duplicate).

Counts for series 1 (total counts (T) 45,850 cpm)
  7615, 7508 cpm
value of T/B (total counts/bound counts)
  6.02, 6.11
Total $T_4$ from FIG. 2
  65, 67 ng/ml or 1625, 1675 pg/tube
Counts from series 2 (total counts 33,000, non-specific counts 300 cpm)
  2534, 2567 cpm Amount bound = Total $T_4$/tube ×

$$\frac{\text{bound counts} - \text{non-specific counts}}{\text{total counts}} = 111.70, 113.35 \text{ pg/tube}$$

Free $T_4$ concentration from FIG. 3 = 1.55, 1.60 ng/ml.

In lieu of estimating the total thyroxine content from the graph as illustrated above, it is possible to substitute an algebraic expression representative of the form of the standard curve described in paragraph (5) based on the counts for series 1.

In the case of thyroxine and any other antibody possessing a single class of binding site the expression is as follows:

$$T_4 \alpha \left( \frac{1}{1 - \frac{B}{T}} \right) \cdot \left( \frac{1}{B} - \frac{1}{B_o} \right)$$

where T is the total count, B is the bound count in that series 1 tube and $B_o$ is the bound count in the series 1 tube corresponding to zero thyroxine concentration.

It is to be noted that the thyroxine concentration is not proportional to 1/B.

EXAMPLE 3

(Indirect $T_3$ assay)

(1) 100 μl samples of standardised sera and unknown sera are pipetted into separate assay tubes in each of two series.

(2) Into each tube of the first series of tubes 100 μl of HEPES buffer containing ANS, 500 μg, and approximately 13,000 cpm of $^{125}$I-labelled $T_3$ is added and the tubes are vortexed and incubated for 30 minutes at room temperature.

(3) 500 μl of Sephadex-anti $T_3$ suspension in HEPES buffer is added to each tube and the tubes are vortexed and incubated at 37° C. for 4 hours. (500 μL of Sephadex-anti $T_3$ suspension contains 62.5 μg of Sephadex coupled to 0.031 μl of $T_3$ antiserum with a $T_3$ binding site concentration of 62.5 fmol.)

(4) After the incubation the tubes are vortexed and centrifuged, aspirated and then washed twice with 2 ml HEPES buffer containing gelatin, 1 g/liter, and TWEEN 20, 1 g/1 liter. The supernatant is decanted and discarded and the bound radioactivity counted.

(5) A standard curve is prepared from the values obtained from the standardised sera and the unknown total triiodothyronine concentrations obtained from this curve.

(6) In parallel with step (2), 100 μl of HEPES buffer containing approximately 13,000 cpm of $^{125}$I-labelled $T_3$ is added to each tube in the second series of tubes and these are then vortexed and incubated for 2 hours at 37° C.

(7) Step (3) is then performed for this series of tubes.

(8) Step (4) is then performed for this series of tubes.

(9) For the standard sera a curve is prepared in which the free $T_3$ concentrations are plotted against the amounts of $T_3$ in the tube which have been bound by Sephadex-anti $T_3$. The amount of $T_3$ bound is computed by multiplying the fraction $^{125}$I-labelled $T_3$ that is bound by the total amount of $T_3$ in the sample. For the unknown sera the total $T_3$ is first determined from step (5), then the amount of $T_3$ bound is computed and the free $T_3$ concentration determined from the standard curve.

Figure 4:
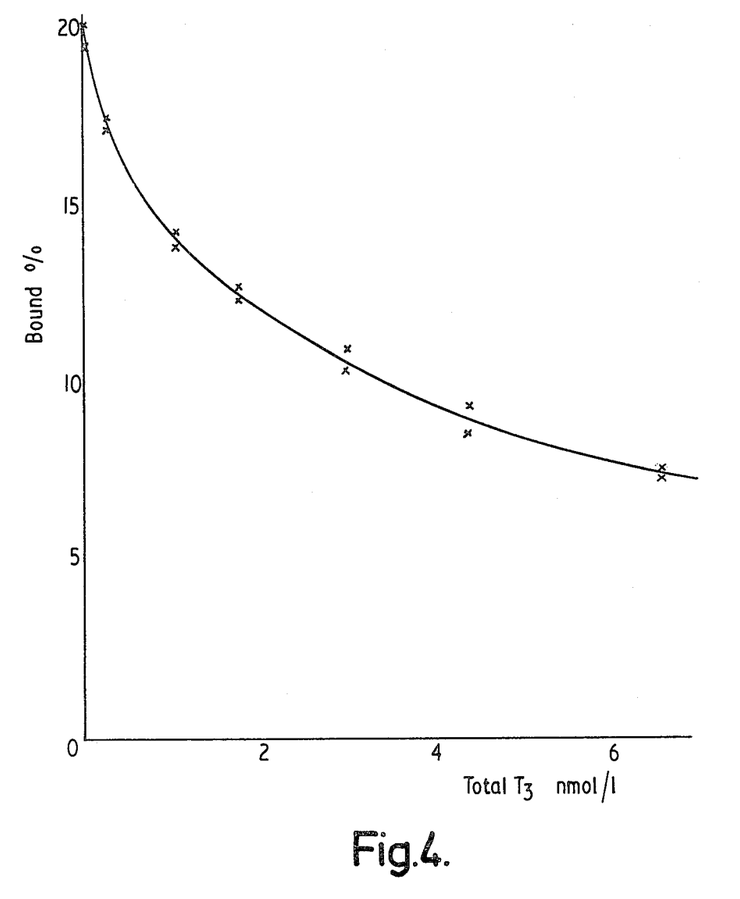

FIG. 4 of the accompanying drawings shows a standard curve for the estimation of total $T_3$, the percent of labelled $T_3$ bound in the series 1 tubes being plotted as ordinate against the known total $T_3$ concentration in the standard solutions, expressed in nmol/l, as abscissa.

Figure 5:
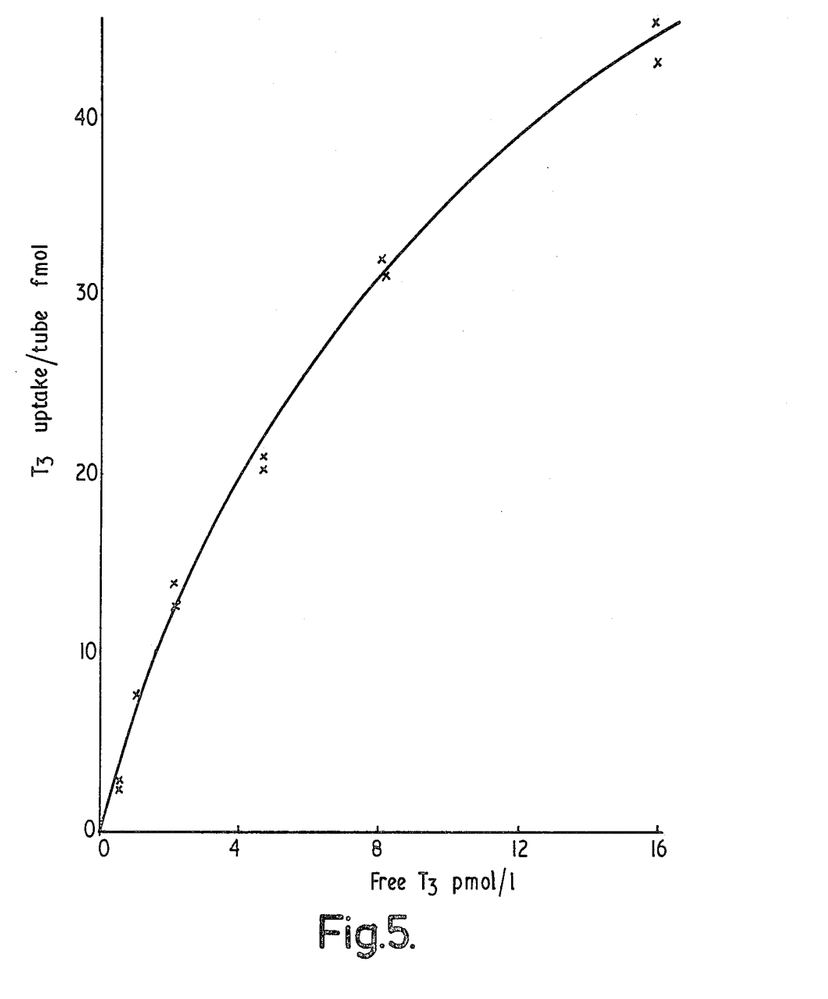

FIG. 5 of the accompanying drawings shows a standard curve for the estimation of free $T_3$, the amount of $T_3$ bound per tube, expressed in fmol, being plotted as ordinate against the known free $T_3$ concentration in the standard solutions, expressed in pmol/l, as abscissa.

The method of calculation is shown for one sample (in duplicate).

Counts for series 1 (total counts 13562 cpm)
1709, 1703 cpm
value of % bound
12.60, 12.56
Total $T_3$ from FIG. 4
1.65, 1.65 nmol/l
Counts from series 2 (total counts in 5 minutes 65,333, non-specific counts in 5 minutes 105)
5271 4954 in 5 minutes Amount bound $\left( = \text{Total } T_3/\text{tube} \times \frac{\text{bound counts} - \text{non-specific counts}}{\text{total counts}} \right)$ 13.05 12.25 fmol/tube Free $T_3$ concentration from FIG. 5
2.4 2.2 pmol/liter.

EXAMPLE 4

(Preparation of stable $T_4$ stock solution)

About 10 mg of L-thyroxine, sodium salt, is dissolved in 10 mls propyleneglycol/water (50:50) rendered alkaline (pH8) with a trace of diethanolamine. A 0.2 ml aliquot is removed, diluted with 2 ml of 0.04 M sodium hydroxide and the extinction at 325 nm is measured against a solvent blank. From the extinction results it is calculated that the concentration of thyroxine in the solution is 9.87 mg/ml.

By dilution using HEPES buffer (and Teflon flasks) a series of standard solutions containing the following concentration of $T_4$ in HEPES buffer (gelatin-free) are prepared: 50, 25, 12.5, 6.25, 3.125 and 1.56 pg/ml.

For use as standard 200 ml aliquots of these solutions are incubated with the amounts of immobilised $T_4$ specified in Example 1 and the procedure of Example 1 is repeated except that each unknown sample is used in an amount of 100 μl.

The results obtained are comparable with those in Example 1.

EXAMPLE 4a

In a slight modification of the procedure of Example 4 $^{131}$I-thyroxine (specific activity approx. 1,000 cpm, from The Radiochemical Centre, Amersham, Bucks) is added to an aliquot of the primary stock solution so as to provide a final (diluted) specific activity of about 10 μCuries/μg. Calculation of the concentration of $T_4$ in the standard solutions prepared by dilution as described above is based instead on observation of the $^{131}$I-activities in these solutions. This modification enables a correction to be made for losses of $T_4$ by absorption on the surfaces of flasks etc.

EXAMPLE 5

Using a succession of steps similar to those described in Example 4 a series of standard solutions containing the following approximate concentration of $T_4$ are prepared: 185, 175, 160, 140, 110, 80, 45 and 25 pg/ml. 1 ml aliquots of each of these solutions are incubated together with the standard amount of antibody described in Example 1 and the procedure of Example 1 is repeated, using 100 μl unknown samples (instead of 25 μl) and incubation at room temperature for 4 hours (instead of 1 hour) to ensure that equilibrium is reached. Following incubation and centrifugation the supernatant solutions are removed from each of the tubes in which standard solution has been used and the concentration of $T_4$ present in each supernatant is determined by a supplementary conventional radioimmunoassay procedure. Meanwhile the separated immobilised antibody precipitates are washed and backtitrated using $^{125}I$-labelled thyroxine as described in Example 1.

The concentration of $T_4$ present in the supernatants as determined by the radioimmunoassay are found to be about 50, 40, 30, 20, 10, 5, 2 and 1 pg/ml, respectively (but were of course accurately determined). These last concentrations are taken as comprising the standard concentrations for calibration purposes. Comparable results are obtained.

EXAMPLE 6

Using a succession of steps identical to Example 4 as modified according to Example 4a, a series of standard solutions containing the same approximate concentrations of $T_4$ as specified at the beginning of Example 4 are prepared, all of which are radioactive. 1 ml aliquots of each of these solutions are incubated together with the standard amounts of antibody as used in Example 1. After 4 hours incubation and centrifugation, the supernatants are removed and the $^{131}I$ $T_4$ radioactivity contained therein is determined. Knowing this and the figure for specific activity the free $T_4$ concentrations in the supernatants can be calculated and used for calibration purposes in the same way as described in Example 5.

It should be noted that the $T_4$ bound to the cellulose-anti $T_4$ includes $^{131}I$-labelled $T_4$ and that the assay of this material involves the use of $^{125}I$-labelled $T_4$. It is therefore necessary to make appropriate corrections for the $^{131}I$-activity by using conventional double isotope counting techniques when carrying out the $^{125}I$ assay.

What is claimed is:

1. A method for indirect measurement of the concentration of a free ligand in a liquid sample also containing the ligand bound to endogenous binding material, comprising the steps of performing two separate measurements, wherein the first measurement is used to determine the total concentration of free and reversibly bound ligand in the sample to be tested, and the second measurement comprises the steps:
   (i) exposing separately to a known amount of labelled ligand (a) the sample to be tested, and (b) each of a plurality of standard solutions containing known concentrations of the free ligand,
   (ii) thereafter exposing each resulting mixture from (i) (a) and (i) (b) separately to an immobilized binding agent to bind a proportion of the free labelled ligand and a similar proportion of the free unlabelled ligand to the immobilized binding agent in each mixture,
   (iii) separating the immobilized binding agent with its bound ligand from the residual material in each mixture,
   (iv) measuring the proportion of labelled ligand bound to the immobilized binding agent in each mixture,
   (v) computing, from this proportion and the total concentration of free and reversibly bound ligand determined in the first measurement, the total amount of ligand bound to the immobilized binding agent in each case, and
   (vi) estimating from this figure the concentration of free ligand in the sample to be tested using as calibration the known concentrations in the standard solutions.

2. A method as claimed in claim 1 wherein the total concentration of free and reversibly bound ligand in the sample to be tested is measured by exposing separately the sample to be tested and each standard solution to a known amount of labelled ligand in the presence of a blocking agent for the reversibly bound ligand, thereafter exposing each resulting mixture separately to immobilised binding agent to bind a proportion of the free labelled ligand and a similar proportion of the free unlabelled ligand to the immobilised binding agent, separating the immobilised binding agent with its bound ligand from the residual material, measuring the proportion of labelled ligand bound to the immobilised binding agent and estimating from this the concentration of free and reversibly bound ligand in the sample to be tested using as calibration the known concentrations in the standard solutions.

3. A method as claimed in claim 1 wherein the blocking agent is 8-anilino-1-naphthalenesulphonic acid and the ligand is thyroid hormone.

4. A method as claimed in claim 1 wherein the sample to be tested is derived from a body fluid of a living creature and the ligand is a compound naturally occurring in free and endogenously-bound form in that fluid.

5. A method as claimed in claim 1 wherein the sample to be tested is derived from a body fluid of a human patient and the ligand is a thyroid hormone selected from thyroxine and triiodothyronine.

* * * * *

UNITED STATES PATENT AND TRADEMARK OFFICE
CERTIFICATE OF CORRECTION

PATENT NO. : 4,381,291

DATED : 4/26/83

INVENTOR(S) : Roger P. Ekins et al.

It is certified that error appears in the above—identified patent and that said Letters Patent are hereby corrected as shown below:

Column 2, line 2, delete "hormones" and insert --hormone--.
Column 3, line 14, delete "radioactivity" and insert --radioactively-.
Column 10, line 1, delete "alternations" and insert --alterations--.
Column 12, line 18, between "B12," and "drugs" insert --and--.
Column 15, line 31, delete "⁄L" and insert --⁄l--.
Column 15, line 38, delete"g/l liter" and insert --g/liter--.
Column 16, line 11, between "65" and "333" delete ",".

Signed and Sealed this

Twenty-third Day of August 1983

[SEAL]

Attest:

GERALD J. MOSSINGHOFF

Attesting Officer         Commissioner of Patents and Trademarks